(12) United States Patent
Hausen

(10) Patent No.: US 8,888,794 B2
(45) Date of Patent: Nov. 18, 2014

(54) MITRAL VALVE TREATMENT

(71) Applicant: Cardica, Inc., Redwood City, CA (US)

(72) Inventor: Bernard A. Hausen, Redwood City, CA (US)

(73) Assignee: Cardica, Inc., Redwood City, CA (US)

(*) Notice: Subject to any disclaimer, the term of this patent is extended or adjusted under 35 U.S.C. 154(b) by 0 days.

(21) Appl. No.: 13/951,873

(22) Filed: Jul. 26, 2013

(65) Prior Publication Data
US 2013/0338684 A1 Dec. 19, 2013

Related U.S. Application Data

(62) Division of application No. 12/817,100, filed on Jun. 16, 2010, now Pat. No. 8,496,671.

(51) Int. Cl.
| A61B 17/10 | (2006.01) |
| A61B 17/064 | (2006.01) |
| A61F 2/24 | (2006.01) |
| A61B 17/00 | (2006.01) |

(52) U.S. Cl.
CPC ............... *A61B 17/10* (2013.01); *A61B 17/064* (2013.01); *A61F 2/24* (2013.01); *A61B 17/0644* (2013.01); *A61B 2017/00243* (2013.01); *A61B 2017/00783* (2013.01); *A61B 2017/0645* (2013.01)
USPC .......................................................... 606/142

(58) Field of Classification Search
USPC ........................... 606/139, 142, 143, 144, 151
See application file for complete search history.

(56) References Cited

U.S. PATENT DOCUMENTS

| 4,586,503 A | 5/1986 | Kirsch et al. |
| 4,932,965 A | 6/1990 | Phillips |
| 4,950,258 A * | 8/1990 | Kawai et al. .................. 604/530 |
| 5,242,457 A | 9/1993 | Akopov et al. |
| 5,891,160 A | 4/1999 | Williamson, IV et al. |
| 6,001,127 A | 12/1999 | Schoon et al. |
| 6,254,615 B1 | 7/2001 | Bolduc et al. |

(Continued)

OTHER PUBLICATIONS

Regarding related patents and patent applications, see the section of the accompanying IDS letter entitled "Related Patents and Patent Applications" for further information.

*Primary Examiner* — Jonathan W Miles
(74) *Attorney, Agent, or Firm* — Cardica, Inc.

(57) ABSTRACT

An exemplary surgical apparatus may include a guide catheter including a clip channel, at least one hook channel, and at least one sling channel defined therein; a clip applier movable within the clip channel, wherein the clip applier holds at least one clip; at least one hook movable within a corresponding hook channel; and at least one sling movable within a corresponding sling channel. An exemplary surgical method for treating a mitral valve may include providing a guide catheter; a clip applier held by the guide catheter, and a clip held by the clip applier; introducing the distal end of the guide catheter into the left atrium; engaging the anterior and posterior leaflets of the mitral valve with the clip; closing the clip; and disengaging the clip applier from the clip, whereby the clip remains in the mitral valve. Another exemplary surgical method for treating a valve may include providing a guide catheter; a clip applier held by the guide catheter, and at least one clip held by the clip applier; advancing the guide catheter into proximity to the valve; and applying at least one clip substantially in the middle of the valve to create two orifices, one on each side of the clip.

7 Claims, 7 Drawing Sheets

(56) References Cited

U.S. PATENT DOCUMENTS

| | | | |
|---|---|---|---|
| 6,409,758 B2 | 6/2002 | Stobie et al. | |
| 6,413,274 B1 | 7/2002 | Pedros | |
| 6,506,197 B1 | 1/2003 | Rollero et al. | |
| 6,695,866 B1 | 2/2004 | Kuehn et al. | |
| 6,726,716 B2 | 4/2004 | Marquez | |
| 6,730,118 B2 | 5/2004 | Spenser et al. | |
| 6,752,813 B2 * | 6/2004 | Goldfarb et al. | 606/139 |
| 6,767,356 B2 | 7/2004 | Kanner et al. | |
| 6,964,684 B2 | 11/2005 | Ortiz et al. | |
| 6,986,775 B2 | 1/2006 | Morales et al. | |
| 7,112,207 B2 * | 9/2006 | Allen et al. | 606/139 |
| 7,223,289 B2 | 5/2007 | Trieu et al. | |
| 7,285,131 B1 | 10/2007 | Bombard et al. | |
| 7,344,544 B2 | 3/2008 | Bender et al. | |
| 7,473,258 B2 | 1/2009 | Clauson et al. | |
| 7,485,142 B2 | 2/2009 | Milo | |
| 7,513,909 B2 | 4/2009 | Lane et al. | |
| 7,658,763 B2 | 2/2010 | Stobie | |
| 7,744,609 B2 * | 6/2010 | Allen et al. | 606/139 |
| 7,758,595 B2 | 7/2010 | Allen et al. | |
| 7,887,583 B2 | 2/2011 | Macoviak | |
| 8,052,748 B2 | 11/2011 | Schoon et al. | |
| 8,070,804 B2 * | 12/2011 | Hyde et al. | 623/2.36 |
| 8,187,299 B2 | 5/2012 | Goldfarb et al. | |
| 8,512,403 B2 | 8/2013 | Navia et al. | |
| 2003/0032981 A1 * | 2/2003 | Kanner et al. | 606/219 |
| 2003/0191479 A1 * | 10/2003 | Thornton | 606/151 |
| 2004/0167620 A1 * | 8/2004 | Ortiz et al. | 623/2.11 |
| 2005/0065601 A1 | 3/2005 | Lee et al. | |
| 2005/0080454 A1 * | 4/2005 | Drews et al. | 606/221 |
| 2005/0267493 A1 * | 12/2005 | Schreck et al. | 606/139 |
| 2006/0064116 A1 * | 3/2006 | Allen et al. | 606/139 |
| 2006/0106456 A9 | 5/2006 | Machold et al. | |
| 2007/0129794 A1 | 6/2007 | Realyvasquez | |
| 2008/0033241 A1 * | 2/2008 | Peh et al. | 600/109 |
| 2008/0051807 A1 * | 2/2008 | St. Goar et al. | 606/139 |
| 2008/0188873 A1 * | 8/2008 | Speziali | 606/144 |
| 2010/0234813 A1 * | 9/2010 | Allen et al. | 604/264 |
| 2011/0190793 A1 * | 8/2011 | Nobles et al. | 606/144 |

* cited by examiner

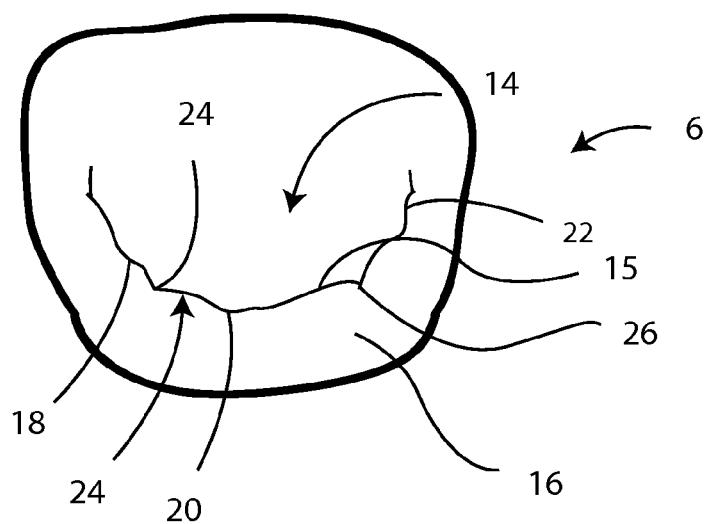
FIG. 2
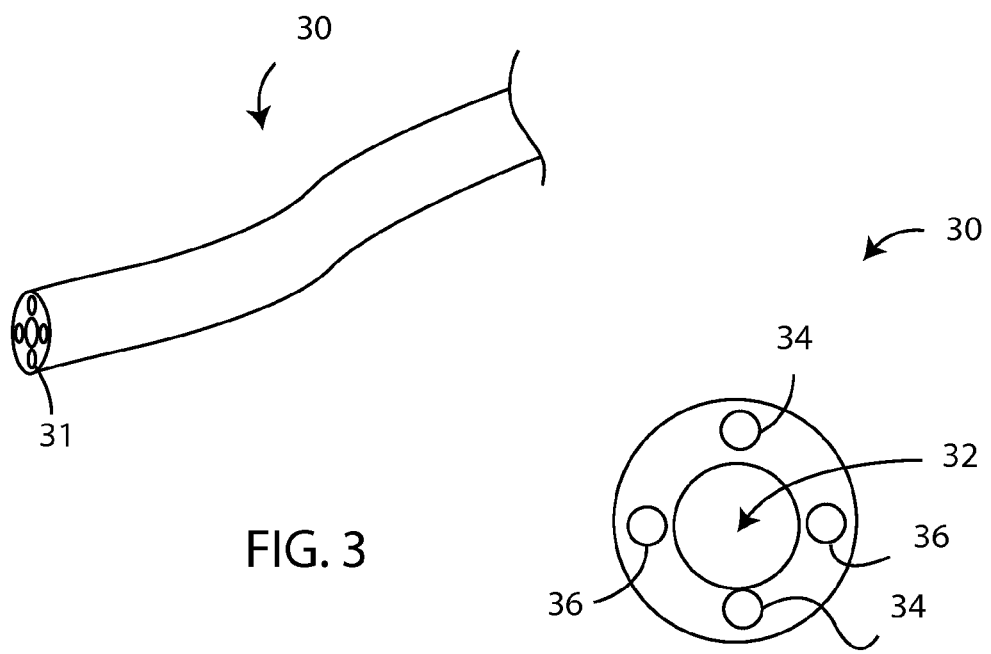
FIG. 3
FIG. 4

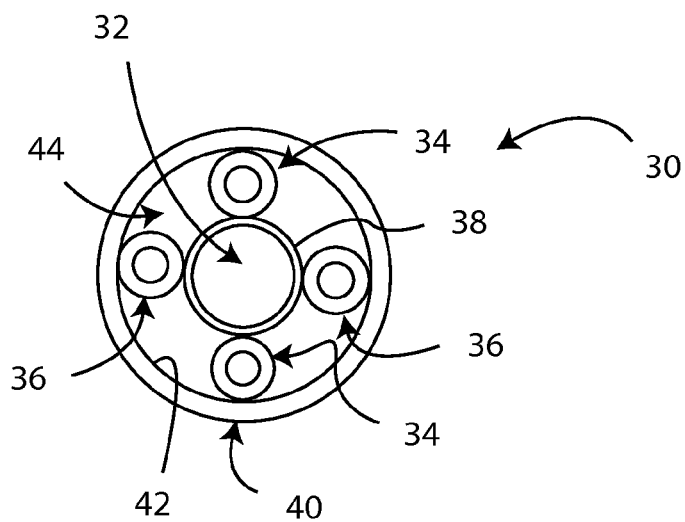
FIG. 5
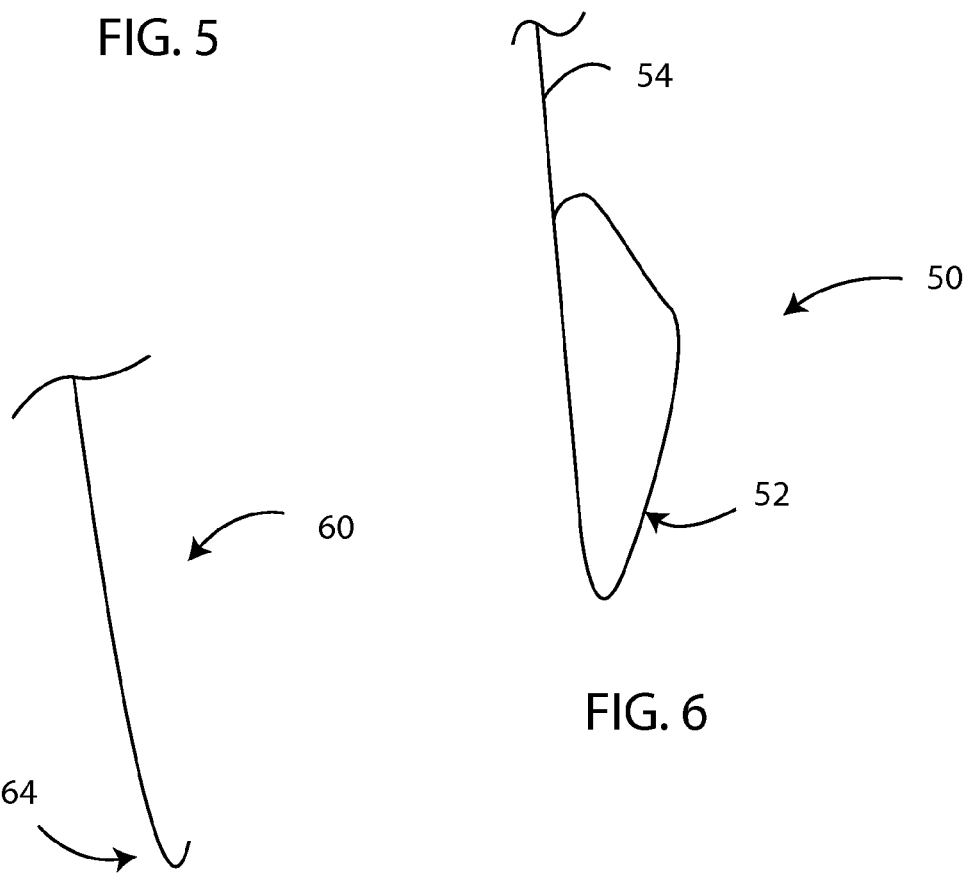
FIG. 6
FIG. 7

MITRAL VALVE TREATMENT

CROSS-REFERENCE TO RELATED APPLICATION

This application is a divisional of U.S. patent application Ser. No. 12/817,100, filed Jun. 16, 2010, which is herein incorporated by reference in its entirety.

FIELD OF THE INVENTION

The invention generally relates to a method and apparatus for treating a heart valve.

BACKGROUND

Referring to FIG. 1, the heart 2 includes a mitral valve 6 that has a valve annulus 4. As a result of age, congenital defect or disease, the mitral valve 6 may fail to close completely when it should during a heartbeat. The normal mitral valve 6 opens when the left ventricle 8 relaxes (diastole), allowing blood from the left atrium 10 to fill the decompressed left ventricle 8. When the left ventricle 8 contracts (systole), the increase in pressure within the left ventricle 8 causes the mitral valve 6 to close, preventing blood from leaking into the left atrium 10 and assuring that all of the blood leaving the left ventricle 8 (the stroke volume) is ejected through the mitral valve 6 into the aorta 12 and then to the body.

Referring to FIG. 2, the mitral valve 6 has two leaflets. The anterior leaflet 14 has a semicircular shape and attached to approximately two-fifths of the perimeter of the valve annulus 4. The free edge 15 of the anterior leaflet 14 is typically continuous, without indentations. The posterior leaflet 16 of the mitral valve 6 is attached to approximately three-fifths of the perimeter of the valve annulus 4. Typically, the posterior leaflet 16 has three segments: the anterior scallop 18, the middle scallop 20, and the posterior scallop 22. The anterior scallop 18 is divided from the middle scallop 20 by a first indentation 24, and the middle scallop 20 is divided from the posterior scallop 22 by a second indentation 26. The indentations 24, 26 aid in posterior leaflet 16 opening during diastole. The free edge 24 of the posterior leaflet 16 contacts the free edge 15 of the anterior leaflet 14 when the mitral valve 6 is closed. The height of the posterior leaflet 16 is typically less than the height of the anterior leaflet 14; however, both leaflets 14, 16 typically have generally similar surface areas.

BRIEF DESCRIPTION OF THE DRAWINGS

FIG. 2 is a top view of a mitral valve of the human heart of FIG. 1.

FIG. 3 is a perspective view of a guide catheter.

FIG. 4 is an end view of the distal end of a first example of the guide catheter of FIG. 3.

FIG. 5 is an end view of the distal end of a second example of the guide catheter of FIG. 3.

FIG. 6 is a perspective view of an exemplary sling.

FIG. 7 is a perspective view of an exemplary hook.

The use of the same reference symbols in different figures indicates similar or identical items.

DETAILED DESCRIPTION

Structure

Figure 1:
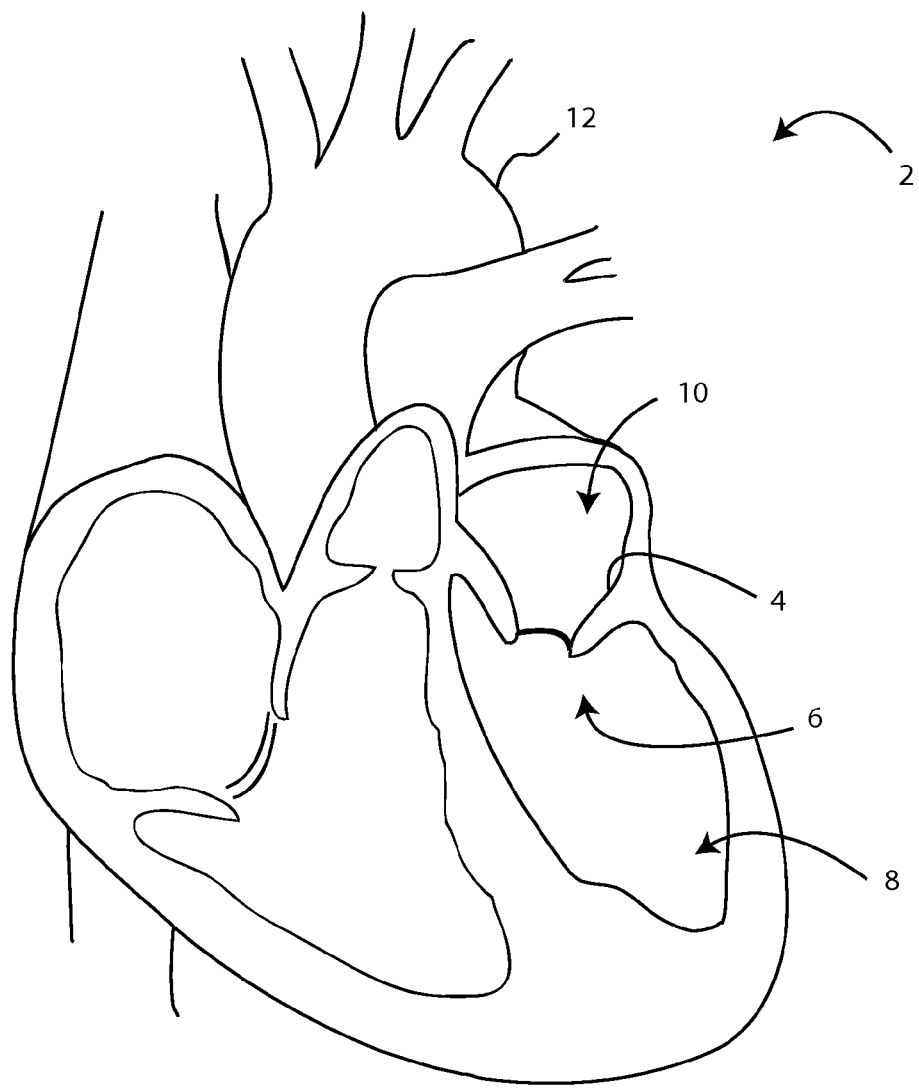
FIG. 1 is a cross-section view of a human heart.

Referring to FIGS. 3-4, an exemplary guide catheter 30 is shown. The guide catheter 30 may be generally cylindrical in shape, and is flexible enough to be advanced through the vasculature of a patient. The surface of the guide catheter 30 is atraumatic, in order to prevent injury to the vasculature of a patient. The guide catheter 30 may be fabricated from any suitable material or combination of materials. The guide catheter 30 may have five channels within. A clip channel 32 may be the largest channel in the guide catheter 30, and may be substantially concentric within the guide catheter 30. The clip channel 32 may be generally cylindrical, with a substantially circular cross-section. However, the clip channel 32 may be shaped differently and/or offset from the longitudinal centerline of the guide catheter 30. Two sling channels 34 may be positioned radially outward from the clip channel 32, on opposed sides of the clip channel 32. Two hook channels 36 may be positioned radially outward from the clip channel 32, on opposed sides of the clip channel 32. The hook channels 36 may be arranged substantially ninety arcuate degrees away from the sling channels 34, such that the channels 34, 36 are substantially evenly spaced around the clip channel 32. However, the channels 34, 36 may be positioned at any other suitable angular positions relative to one another; and the channels 32, 34, 36 as a group may be arranged in any other suitable manner.

As one example, referring to FIG. 4, one or more of the channels 32, 34, 36 may be lumens defined within a solid or partially solid guide catheter 30. If so, any such channel may be fabricated within the guide catheter 30 in any suitable manner, such as by drilling, boring, or laser-cutting, or the guide catheter 30 may be fabricated in such a manner that any such channel is devoid of material within throughout the fabrication process. As another example, referring to FIG. 5, one or more of the channels 32, 34, 36 may be individual tubes positioned within the guide catheter 30. If so, the channels 34, 36 may be positioned between the outer surface 38 of the clip channel 32 and the inner surface 42 of an outer sheath 40. In this way, the channels 34, 36 also may support the clip channel 32 within the lumen 44 of the outer sheath 44. The channels 32, 34, 36 may be connected to the outer sheath 40 in any suitable manner. As another example, the guide catheter 30 may be fabricated in any other suitable manner that results in a suitable number of channels defined therethrough.

Referring to FIG. 6, at least one sling 50 may be utilized in conjunction with the guide catheter 30. Each sling 50 may include a broad section 52 and an extension 54 extending proximal to the broad section 52. The broad section 52 may be substantially D-shaped, as shown in FIG. 6, or may have any other suitable shape. The broad section 52 may be a closed loop, or may be open at least in party. The broad section 52 may lie in substantially a single plane, but need not do so. The sling 50 may be fabricated from one or more pieces of superelastic wire, such as wire composed of nickel-titanium alloy. However, the sling 50 may be fabricated from spring steel or other metal that is not superelastic, or may be fabricated from any suitable nonmetallic material. The extension 54 is configured to extend through a corresponding sling channel 34 in the guide catheter 30. The sling 50 is collapsible, such that the sling 50 in its entirety can be held partially or completely within a corresponding sling channel 34 in an initial position, as described in greater detail below.

Referring to FIG. 7, at least one hook 60 may be utilized in conjunction with the guide catheter 30. Each hook 60 may be curved or angled at the distal end thereof, such that the free end of the hook 60 is oriented at least partially in the proximal direction. The hook 60 may be J-shaped, or may be shaped in any other suitable manner. The hook 60 may be fabricated from one or more pieces of superelastic wire, such as wire composed of nickel-titanium alloy. However, the hook 60 may be fabricated from spring steel or other metal that is not superelastic, or may be fabricated from any suitable nonmetallic material. The proximal end of the hook 60 is configured to extend through a corresponding hook channel 36 in the guide catheter 30. The hook 60 is collapsible, such that the hook 60 can be held partially or completely within a corresponding hook channel 36 in an initial position, as described in greater detail below. One or more hooks 60 may include a closing or locking feature at the distal end thereof that can be automatically or remotely actuated to open and close as needed.

Figure 8:
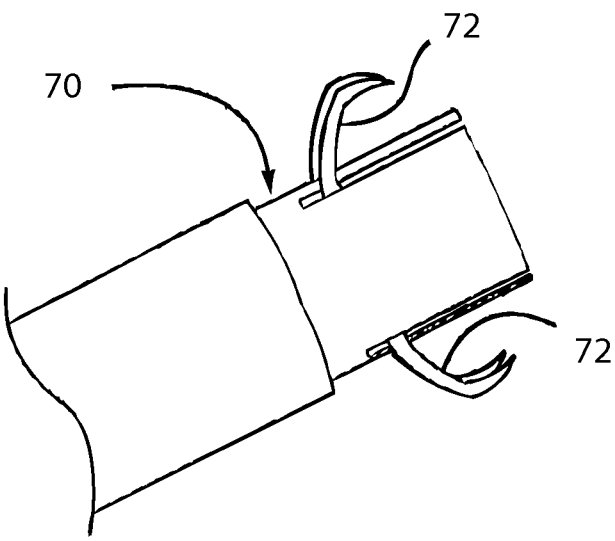
FIG. 8 is a perspective view of an exemplary clip applier.
Figure 9:
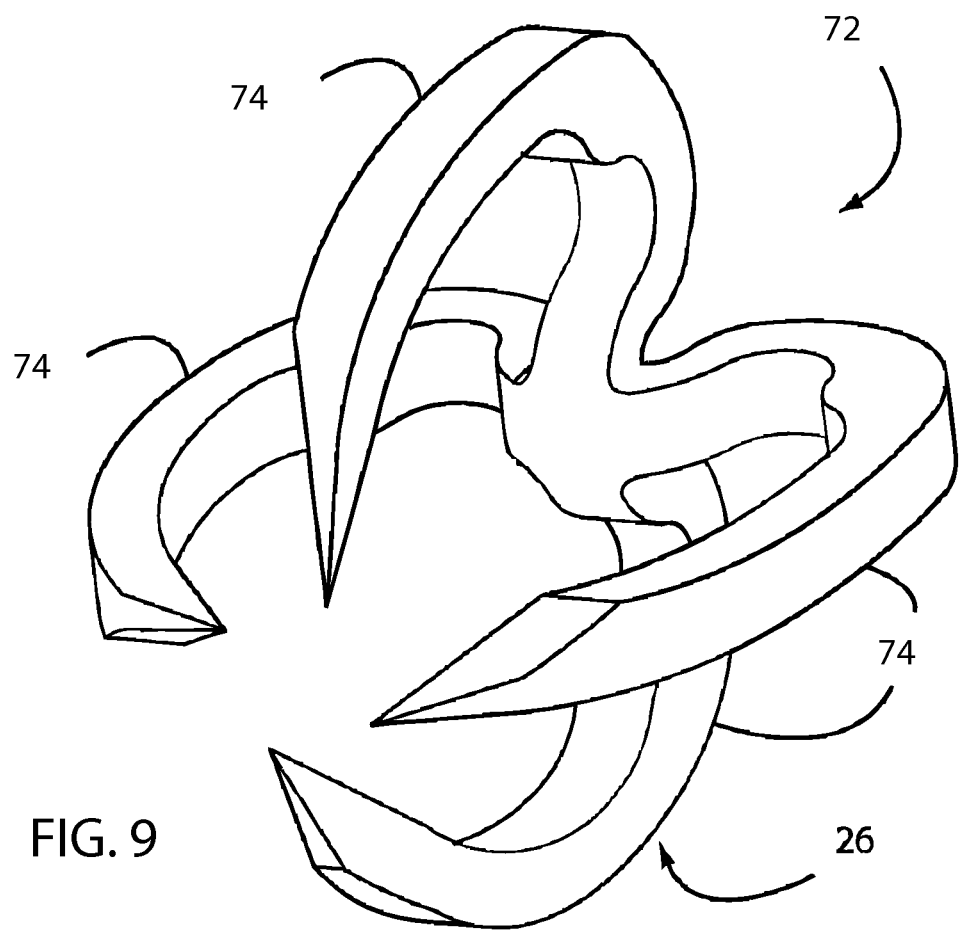
FIG. 9 is a perspective view of an exemplary clip.

A clip applier may be utilized in conjunction with the clip channel 32. As one example, the clip applier may be substantially as set forth in U.S. Pat. App. Pub. No. 2009/0093826 of Warder-Gabaldon et. al., filed on Oct. 5, 2007 (the "Clip Publication"), which is hereby incorporated by reference in its entirety. Referring to FIG. 8, the clip applier 70 may be configured to splay and then deploy a clip 72, as set forth in the Clip Publication. Referring to FIG. 9, the clip 72 may have four tines 74 arranged in an X configuration. However, the clip 72 may have tines 74 arranged in any other suitable configuration, and/or may include a different number of tines 74. The clip applier 70 is configured to be held partially or completely with the corresponding clip channel 32 of the guide catheter 30 in an initial position, as described in greater detail below.

Operation

Figure 10:
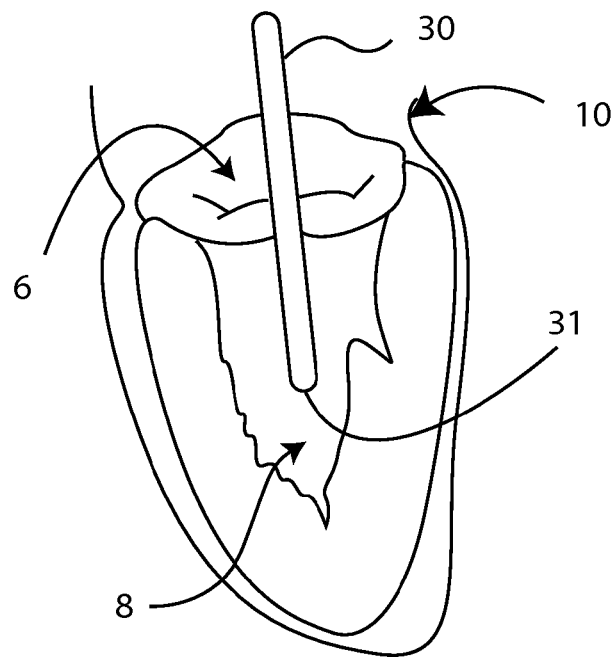
FIG. 10 is a perspective view of a step of a method of treating the mitral valve.

Referring to FIG. 10, the distal end 31 of the guide catheter 30 is advanced through the left atrium 10 into the left ventricle 8, through the mitral valve 6. The guide catheter 30 may be introduced into the left atrium 10 through a transseptal puncture, through the patient's vasculature, or in any other suitable manner that provides access to the left atrium 10 for the guide catheter 30. The heart 2 advantageously continues to beat during and after introduction of the guide catheter 30 thereinto; however, the heart 2 may be stopped and the patient placed on a heart-lung machine at the discretion of the user.

Figure 11:
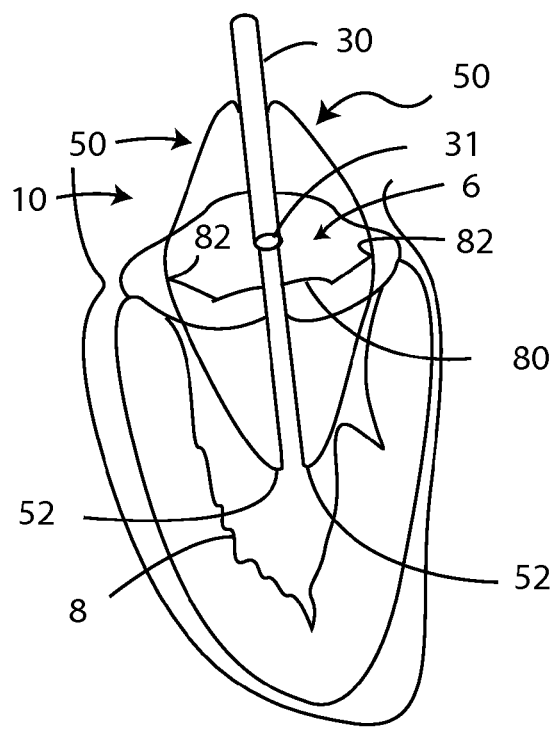
FIG. 11 is a perspective view of another step of a method of treating the mitral valve.

After the distal end 31 of the guide catheter 30 has been introduced into the left ventricle 8, then one or more slings 50 are each advanced distally out of the corresponding sling channels 34 in the guide catheter 30. Such advancement may be performed in any suitable manner, such as by pushing the extension 54 distally either by hand or by application of force through a handle (not shown). The broad section 52 of each sling 50 is initially compressed by and constrained by contact with the interior of the corresponding sling channel 34 such that each sling 50 can be held within the circumference of the guide catheter 30. As each sling 50 advances distally, its broad section 52 advances out of the corresponding sling channel 34 such that the broad section 52 is no longer constrained by the corresponding sling channel 34. At that time, the broad section 52 self-expands within the left ventricle 8. Alternately, the guide catheter 30 actively expands each broad section 52 within the left ventricle 8. Referring to FIG. 11, advantageously two slings 50 are deployed from the guide catheter 30 and expanded. The slings 50 expand from the left ventricle 8 through the mitral valve 6 and into the left atrium 10. In this way, the slings 50 generally center the guide catheter 30 within the mitral valve 6. The guide catheter 30 may then be retracted such that its distal end 31 is positioned in the left atrium 10. During that retraction of the guide catheter 30, the slings 50 substantially remain in position relative to the left ventricle 8, mitral valve 6 and left atrium 10 due to the outward force exerted by the slings against the inner surfaces of the left ventricle 8 and the left atrium 10, as well as the lateral ends 82 of the opening 80 of the mitral valve 6. The guide catheter 30 slides along the extensions 54 of the slings 50 as the broad sections 52 of the slings 50 remain generally in place in the heart 2. The guide catheter 30 may be retracted using ultrasound, fluoroscopy, or any other suitable imaging method to determine the location of the distal end 31 of the guide catheter 30.

Next, one or more hooks 60 are each advanced distally out of the corresponding hook channels 34 in the guide catheter 30. Such advancement may be performed in any suitable manner, such as by pushing each hook 60 distally either by hand or by application of force through a handle (not shown). The distal J-portion 64 of at least one hook 60 may be narrower than the corresponding hook channel 36 in the guide catheter 30, such that the J-portion 64 of at least one hook 60 is not substantially compressed while that hook 60 is in its initial position within the hook channel 36 in the guide catheter 30. Alternately, the J-shaped portion 64 of at least one hook 60 may be wider than the corresponding hook channel 36, such that the J-shaped portion 64 is initially compressed by and constrained by contact with the interior of the corresponding hook channel 36 such that each J-shaped portion 64 can be held within the circumference of the guide catheter 30. As each hook 60 advances distally, the J-shaped portion 64 of each hook 60 advances out of the corresponding hook channel 36 in the guide catheter 30. The hook 64 may simply move out of the hook channel 36 without substantially changing its size or shape. Alternately, where the hook channel 36 initially constrained the J-shaped portion 64 of at least one hook 60, motion of the J-shaped portion 64 of that hook or hooks 60 out of the corresponding hook channel 36 may allow the J-shaped portion 64 to self-expand, and/or frees the J-shaped portion 64 to allow the guide catheter 30 to actively expand it. As the hooks 60 are advanced, they pass through the mitral valve 6 and entire the left ventricle 8. Because each hook 60 has a J-shaped portion 64 or similarly shaped portion at the distal end thereof, the distal end of each hook 60 is substantially blunt, and thereby passes through the mitral valve 6 without engaging or damaging the tissue of the mitral valve 6.

Next, the physician retracts one of the hooks 60, causing each retracted hook 60 to grab the edge of a corresponding leaflet 14, 16 of the mitral valve 6. This may require multiple attempts, and may be controlled using ultrasound, fluoroscopy, or any other suitable imaging device or technique. Either leaflet 14, 16 may be engaged first. For purposes of describing the method, and not to limit the order of engagement, it is assumed in this document that the physician chooses to engage the anterior leaflet 14 first. Once that hook 60 has engaged the anterior leaflet 14, the hook 60 is retracted toward the guide catheter 30, moving the edge of the anterior leaflet 14 to its closed position—that is, the position the anterior leaflet 14 would assume during normal closure of the mitral valve 6. Optionally, the hook 60 may include a locking feature (not shown) that allows the physician to manually lock the J-shaped portion 64 of the hook 60 after it engages the anterior leaflet 14, or may include an automatic locking feature that automatically locks the J-shaped portion 64 of the hook 60 after it engages the anterior leaflet 14. Such a locking feature would prevent the leaflet 14 from disengaging from the hook 60.

Figure 12:
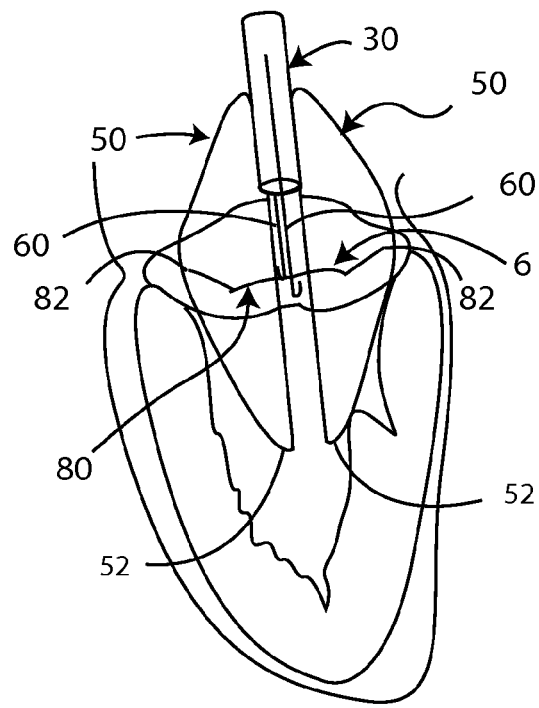
FIG. 12 is a perspective view of another step of a method of treating the mitral valve.

Next, the posterior leaflet 16 may be engaged with a second hook 60 in substantially the same manner in which the anterior leaflet 14 was engaged, as described above. The hook 60 is retracted toward the guide catheter 30, moving the edge of the posterior leaflet 16 to its closed position—that is, the position the posterior leaflet 16 would assume during normal closure of the mitral valve 6. Alternately, the hooks 60 can be manipulated substantially simultaneously to engage leaflets 14, 16 at substantially the same time, rather than sequentially as described above. Referring also to FIG. 12, the hooks 60 thereby hold the leaflets 14, 16 in a closed position that mimics the position in which the leaflets 14, 16 would be held by a clip. The physician may utilize ultrasound, fluoroscopy, or any other suitable imaging technique, and/or a nonimaging technique such as flow measurement, to view and/or measure the mitral valve 6 and determine the impact of fixing the leaflets 14, 16 in substantially the position in which they are held by the hooks 60. If the imaging and/or measurement does not indicate sufficient reduction of mitral insufficiency, the physician can release the leaflets 14, 16 from the hooks 60, such as by moving the hooks 60 distally. The physician may then reorient the guide catheter 30 and capture the leaflets 14, 16 again, as described above, where the hooks 60 engage different portions of the leaflets 14, 16.

Optionally, the slings 50 may stretch the opening 80 of the mitral valve 6 by moving the ends 82 of the opening 80 away from one another. By stretching the mitral valve 6, the leaflets 14, 16 may move closer to one another, rendering it easier to capture them with the hooks 60. The broad sections 52 of the slings 50 may form substantially a single plane, where the sling channels 34 are oriented substantially along a line that includes the centerline of the guide catheter 30. The hook channels 36 may be oriented along a line that includes the centerline of the guide catheter 30, where that line is substantially perpendicular to the line formed by the sling channels 34 and the centerline of the guide catheter 30. In this way, the hook channels 36 and sling channels 34 may be substantially evenly spaced along ninety-degree increments along the circumference of the guide catheter 30. Further, in this way the hooks 60 may be oriented relative to the opening 80 in the mitral valve 6 in a manner that maximizes the ease of engagement between the hooks 60 and the leaflets 14, 16.

Figure 13:
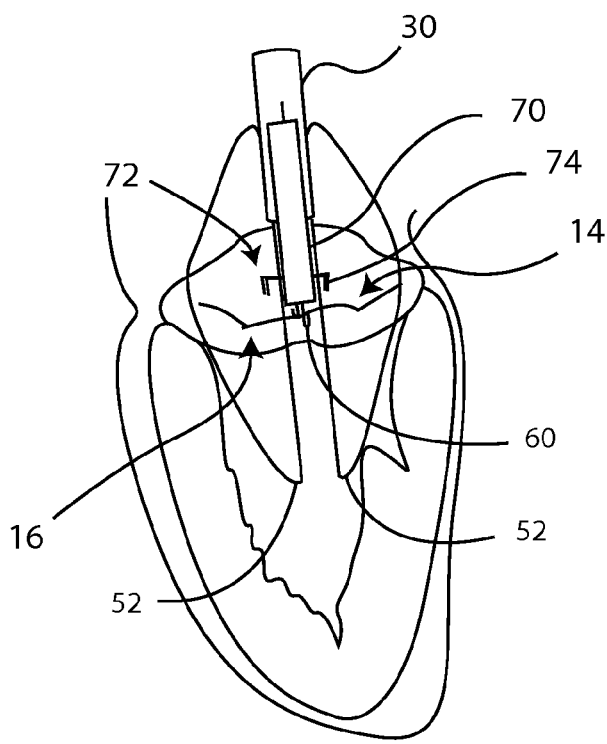
FIG. 13 is a perspective view of another step of a method of treating the mitral valve.

Once the physician is satisfied with the alignment of the edges of the leaflets 14, 16, the clip applier 70 is advanced distally along the clip channel 32 of the guide catheter 30, at least partially out of the distal end 31 of the guide catheter 30. The clip applier 70 is then actuated to splay the clip 72, as described in the Clip Publication. The distal ends of the tines 74 of the clip 72 each move in a direction having a component of motion away from the longitudinal centerline of the clip 72. This deformation of the clip 72 may be referred to as "splaying." Advantageously, the clip 72 is plastically deformed during splaying, such that after splaying the tines 74 of the clip 72 remain in the splayed configuration on their own, without requiring the application of force from the clip applier 70 to maintain the tines 74 in the splayed configuration. Alternately, the clip 72 may be splayed in an elastic or superelastic manner. The splayed clip 72 is still held by the clip applier 70, and the distal ends of the tines 74 extend radially outward beyond the outer perimeter of the clip applier 70 and of the guide catheter 30. Next, referring also to FIG. 13, the leaflets 14, 16 and the splayed clip 72 are brought into contact with one another. This may be performed by moving the clip applier 70 distally, thereby penetrating the distal ends of at least two tines 74 into the leaflets 14, 16. As another example, the hooks 60 may be retracted proximally, bringing the leaflets 14, 16 into contact with the tines 74 and causing the tines 74 to penetrate the leaflets 14, 16. As another example, the clip applier 70 may be moved distally and the hooks 60 may be moved proximally in order to penetrate the tines 74 through the leaflets 14, 16. Advantageously, all of the tines 74 penetrate the leaflets 14, 16. However, because the clip 72 has multiple tines 74, it is not necessary for all of the tines 74 to penetrate the leaflets 14, 16; rather, one or more tines 74 may enter the opening 80 in the mitral valve 6. Alternately, the clip 72 may be configured to have two tines 74, and the clip applier 70 may be actuated in a manner that ensures that one tine 74 penetrates each leaflet 14, 16.

Figure 14:
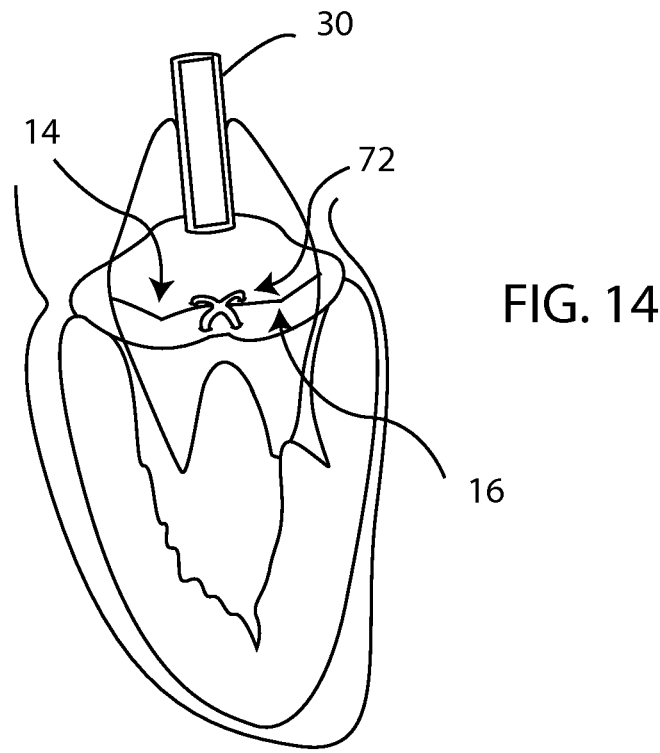
FIG. 14 is a perspective view of another step of a method of treating the mitral valve.
Figure 15:
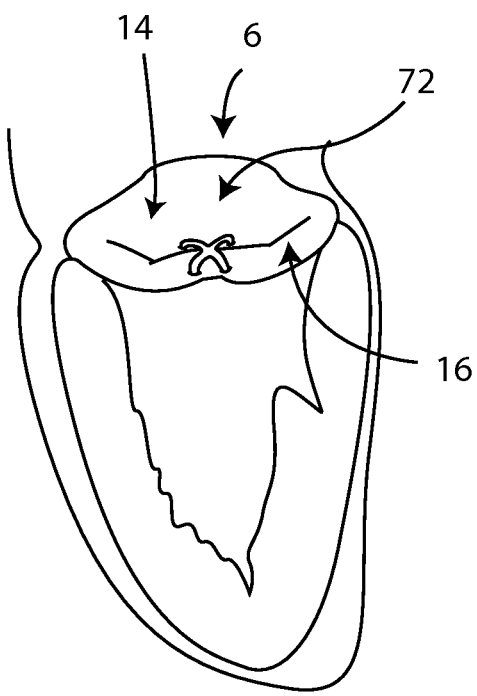
FIG. 15 is a perspective view of a treated mitral valve with a clip holding the leaflets thereof.

Next, the clip 72 is closed, substantially as described in the Clip Publication. As a result, the leaflets 14, 16 are firmly and permanently connected together by the clip 72. Advantageously, the clip 72 engages the leaflets 14, 16 approximately at the center of the mitral valve 6. However, the clip 72 may be placed at any location along the leaflets 14, 16, at the discretion of the physician. Before the closed clip 72 is released from the clip applier, the physician can retract the clip applier 70 proximally a small amount, to ensure that the clip 72 has penetrated the leaflets 14, 16 and firmly attached them. Referring also to FIG. 14, after the physician is satisfied that the clip 72 has closed firmly into the tissue of the leaflets 14, 16, the clip applier 70 releases the closed clip 72, substantially as described in the Clip Publication. The clip applier 70 is then withdrawn proximally, partially or completely into the clip channel 32 in the guide catheter 30. The hooks 60 are released from the leaflets 14, 16 in any suitable manner and withdrawn into the hook channels 36 in the guide catheter. Referring also to FIG. 15, the guide catheter 30 is then withdrawn, leaving the closed clip 72 in the mitral valve 6. A double orifice mitral valve 6 has thus been created, which is suitable for treating mitral insufficiency.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. For example, other heart valves or bodily valves than the mitral valve 6 may be treated with the apparatus and method described above. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:
1. A surgical apparatus, comprising:
   a guide catheter including a clip channel, at least one hook channel, and at least one sling channel defined therein;
   a clip applier movable within said clip channel, wherein said clip applier holds at least one clip;

at least one hook movable within a corresponding said hook channel; and at least one sling movable within a corresponding said sling channel.

2. The surgical apparatus of claim 1, wherein said hook channels and said sling channels are alternately positioned and substantially evenly spaced about the perimeter of said guide catheter.

3. The surgical apparatus of claim 1, wherein each said hook channel and each said sling channel is positioned radially outward from said clip channel.

4. The surgical apparatus of claim 1, wherein said guide catheter is a tube with a lumen defined therein; wherein at least one of said hook channels and said sling channels is a discrete tube positioned within said lumen of said guide catheter.

5. The surgical apparatus of claim 1, wherein at least one sling includes a generally D-shaped broad section.

6. The surgical apparatus of claim 1, wherein said clip has at least three tines.

7. The surgical apparatus of claim 1, wherein said clip is splayable.

* * * * *